United States Patent [19]

Kawada et al.

[11] 4,069,335
[45] Jan. 17, 1978

[54] AGRICULTURAL GERMICIDAL COMPOSITION

[75] Inventors: Seigo Kawada, Fujieda; Nobuya Ohta; Akira Sakamoto, both of Shizuoka, all of Japan

[73] Assignee: Kumial Chemical Industry Co., Ltd., Tokyo, Japan

[21] Appl. No.: 661,152

[22] Filed: Feb. 25, 1976

[51] Int. Cl.² .......................... A01N 9/22; A01N 9/24
[52] U.S. Cl. ..................................... 424/274; 424/324
[58] Field of Search ................................ 424/324, 274

[56] References Cited

U.S. PATENT DOCUMENTS

| 2,553,770 | 5/1951 | Kittleson | 424/151 X |
| 3,178,447 | 4/1965 | Kohn | 424/274 X |

OTHER PUBLICATIONS

Chemical Abstracts 71:49619p (1969).

*Primary Examiner*—Leonard Schenkman
*Attorney, Agent, or Firm*—Oblon, Fisher, Spivak, McClelland & Maier

[57] ABSTRACT

An agricultural germicidal composition, which comprises a benzanilide of the formula:

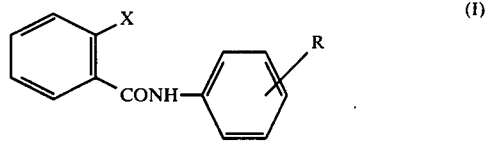

(I)

wherein X represents halogen or methyl and R represents hydrogen, $C_{1-5}$ alkyl or $C_{1-5}$ alkoxy and a phthalimide of the formula

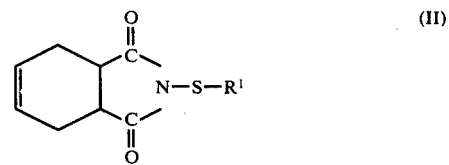

(II)

wherein $R^1$ represents a polyhaloalkyl group as active ingredients for the treatment of plant, soil and seed diseases.

8 Claims, No Drawings

AGRICULTURAL GERMICIDAL COMPOSITION

BACKGROUND OF THE INVENTION

1. Field of the Invention

The present invention relates to agricultural germicidal compositions which are effective for inhibiting seed diseases, soil diseases and plant diseases economically.

2. Description of the Prior Art

The diseases of seeds, soils, crop plants and fruits, especially seed diseases and soil diseases are caused by pathogenic microorganisms such as Basidiomycetes, e.g., *Rhizoctonia Solani;* Fungi Imperfecti, e.g., Fusarium sp. and other disease germs, e.g., Pythium sp., *Typhula incarnate,* Verticillium sp., Aphanomyces sp., Sclerotinia sp. and Phytophthora and the like. Heretofore, organic mercury compounds such as ethylmercuric phosphate, 2-methoxyethylmercuric chloride have been used as agricultural germicides for seed diseases and soil diseases. However, because organic mercuric compounds adversely effect the central nervous system and splanchnic organs, e.g., hepatopathia, the use of the compounds has been prohibited. On the other hand, bis-(dimethylthiocarbamoyl)disulfide (TMTD), methyl N-[1-(butylcarbamoyl)2-benzimidazol]carbamate (Benomyl), pentachloronitrobenzene (PCNB) and the like have been used instead of the organic mercury compounds. However, these compounds have disadvantages in that they are effective only for some pathogenic microorganisms, they possess phytotoxicity and their germicidal effects are adversely influenced by unsatisfactory durability. These compounds do not possess the germicidal effects of the organic mercury compounds. A need therefore, continues to exist for agricultural germicides which effectively inhibit these diseases.

SUMMARY OF THE INVENTION

Accordingly, one object of the present invention is to provide an agricultural germicide with improved effectiveness against seed, plant and soil diseases.

This object and other objects of the present invention can be attained by agricultural germicidal compositions which comprise a benzanilide having the formula:

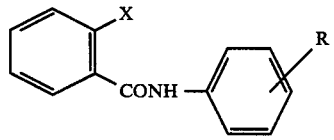

wherein X represents halogen or methyl and R represents hydrogen, alkyl or alkoxy, and a phthalimide having the formula

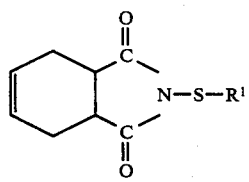

wherein R¹ represents a polyhaloalkyl group.

DETAILED DESCRIPTION OF THE PREFERRED EMBODIMENTS

The benzanilide compounds (I) can be prepared by either of the following reactions:

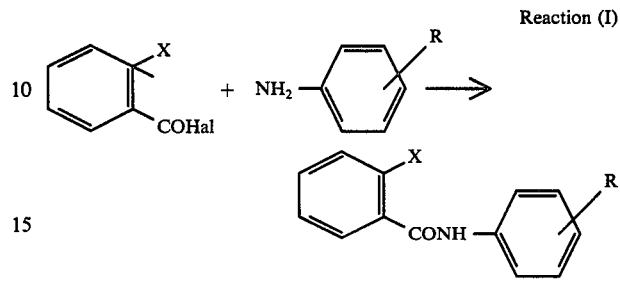

Reaction (I)

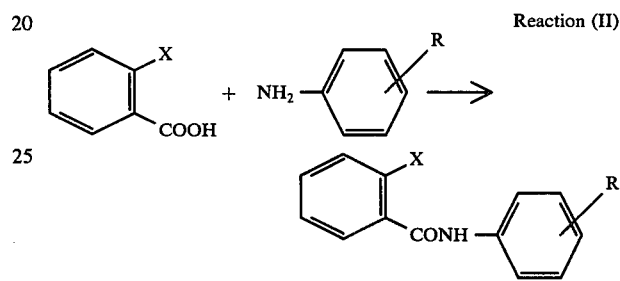

Reaction (II)

wherein X represents $CH_3$ or halogen and Hal represents halogen and R is defined as above.

In Reaction (I), suitable dehydrohalogenating agents include tertiary amines, such as triethylamine, dimethylaniline and pyridine; and alkali agents such as sodium carbonate, sodium bicarbonate, and the like. It is also possible to simply use twice the stoichiometric amount of the aniline compound as the dehydrohalogenating agent.

The reaction solvent can be any solvent so long a it is inert to the o-methylbenzoylhalide or the aniline compound. Thus, suitable solvents include benzene, toluene, acetone, ether, dioxane, acetonitrile and the like. The reaction temperature can be set between $-20 \sim 100°$ C.

In reaction (II), the compounds of the invention can be prepared by adding a dehydrating agent to a mixture of o-toluic acid and the aniline compound in the presence or in the absence of a base in a one-step reaction. Reaction (II) is the most advantageous reaction from the industrial operation point of view to obtain benzanilide compounds of high purity and in high yield. In reaction (II), suitable dehydrating agents include phosphorus oxychloride, phosphorus trichloride, phosphorus pentchloride, phosphorus tribromide, thionyl chloride, sulfuryl chloride, sulfonic acid, sulfuric acid, hydrogen halide, carbodiimides, alumina and silica. Suitable bases include tertiary amines such as trimethyl amine and pyridine; carbonates such as sodium carbonate and sodium bicarbonate; and alkali hydroxides such as sodium hydroxide. Suitable reaction solvents include benzene, toluene, xylene, chlorobenzene, acetone, methylethylketone, ether, dioxane, tetrahydrofuran, dimethyl formamide, acetonitrile, chloroform, carbon tetrachloride, and the like. The reaction temperature can be $-20 \sim 200°$ C and the reaction time may be 1 - 20 hours.

The inventors have studied the agricultural germicidal effect of the benzanilides having the formula (I) and have found that the compositions obtained by combining a benzanilide of formula (I) and a phthalimide of formula (II) exhibit substantially greater effects for the inhibition of seed and soil diseases as well as exhibiting a broader antimicrobial spectrum in comparison to the benzanilide compounds themselves. From the viewpoint of the amounts of the active ingredients, the amount of the benzanilide of formula (I) in the composition can be decreased to about 1/20 to ½ and the amount of the phthalimide of formula (II) can be decreased to about 1/20 to ½.

From the antimicrobial spectrum viewpoint, the benzanilides of formula (I) exhibit substantial effects against *Rhizoctonia Solani, Corticium Rolfsii, Typhula Incarnata,* but on the other hand, their effectivenss against Phythium sp., Fusarium sp., Verticillium sp., Aphanomyces sp., Sclerotinia sp., Phytophthora, and the like is substantially less. On the other hand, the phthalimides of formula (II) are effective against Phthium sp. and Phytophthora, but are not nearly as effective against *Rhizoctonia Solani, Fusarium* sp., *Corticium Rolfsii, Typhula Incarnata, Verticillium* sp., Aphanomyces sp. and Sclerotinia sp. However, all of the diseases caused by the above-mentioned pathogenic microorganisms can be inhibited by applying the composition of the present invention which is the combination of benzanilide (I) and phthalimide (II).

As a result of the present invention, the usual seed disinfection work and soil disease inhibiting work can be substituted by a method of only using one seed treatment to inhibit the diseases, therefore requiring much less labor. It is also possible to inhibit various diseases such as Sheath blight, bean rust and the like as well as the above-described seed and soil diseases.

The compositions of the invention comprise the benzanilide of formula (I) and the phthalimide of formula (II) in a ratio ranging from 1 : 0.1–10, preferably 1 : 0.25 – 3. When the agricultural germicidal composition of the invention is applied by the seed treatment method, the composition is used in a ratio of 0.1 – 50 g, preferably 0.5 – 5 g of the active ingredients per 1 of the seeds. When the agricultural germicidal composition of the invention is applied by the soil mixing or soil drench and injection treatment method, the composition is used in an amount of 0.05 – 10.0 kg, preferably 0.5 – 2.0 kg of the active ingredients per 10 ares. When the agricultural germicidal composition of the invention is applied by the spray treatment method, the composition is used by spraying 20 – 2000 ppm, preferably 100 – 500 ppm of a dilute solution of the active ingredients to the plants to inhibit the agricultural plant, seed and soil diseases. The typical active ingredients used in the agricultural germicidal compositions will now be illustrated.

Benzanilides of formula (I)

Compound 1: 3'-methyl-2-chlorobenzanilide m.p. 124° C

Compound 2: 3'-methoxy-2-bromobenzanilide m.p. 162°–164° C

Compound 3: 2-iodobenzanilide m.p. 144°–145° C

Compound 4: 3'-isopropoxy-2-iodobenzanilide m.p. 94°–96° C

Compound 5: 2'-ethyl-2-methylbenzanilide m.p. 125° C

Compound 6: 3'-isopropoxy-2-methylbenzanilide m.p. 92–94° C

Compound 7: 3'-sec.-butoxy-2-methylbenzanilide m.p. 75°–77° C

Compound 8: 3'-tert-pentyl-2-methylbenzanilide m.p. 68°–71° C

Phthalimides of formula (II)

Compound A: N-trichloromethylthio-3a,4,7,7a-tetrahydrophthalimide

Compound B: N-1,1,2,2-tetrachloroethylthio-3a,4,7,7a-tetrahydrophthalimide

Suitable forms of the agricultural germicidal compositions of the invention include solutions, emulsions, wettable powders, fine granules, granule dust, flowable suspension pastes, microcapsules and the like. However, the combined active ingredients alone may be applied. These compositions may be prepared by conventionally mixing the active ingredients with an inert diluent or an inert carrier, and if necessary, with an emulsifier or a dispersing agent. Suitable solid diluents or carriers include talc, kaolin, clay, diatomaceous earth, hydrated silica, vermiculite, wood powder or the like. Suitable liquid diluents or carriers include water, alcohols such as methanol and propanol; ketones such as acetone and cyclohexanone; aromatic hydrocarbons such as toluene, xylene, benzene and methyl naphthalene; polar solvents such as dimethyl sulfoxide and dimethylformamide, petroleum type media such as paraffin and the like.

Suitable emulsifiers and dispersing agents include polyoxyethylene alkylaryl ether, polyoxyethene esters of aliphatic carboxylic acids, polyoxyethylene ethers of aliphatic alcohol, sodium alkylbenzenesulfonate, calcium dinaphthylmethane-disulfonate, sodium lignin sulfonate, alkyl dimethyl benzyl ammonium chloride, polyvinyl alcohol, carboxymethyl cellulose or the like.

Certain examples of the agricultural germicidal compositions of the invention will be illustrated.

Composition No. 1 Dust:

25 Wt. parts of Compound No. 6, 25 wt. parts of Compound A, 0.4 wt. part of tall oil fatty acid, 0.5 wt. part of hydrated silica and 49.1 wt. parts of fine clay were uniformly mixed and crushed to give a dust composition.

Composition No. 2 Wettable powder:

25 Wt. parts of Compound No. 7, 25 wt. parts of Compound A, 2 wt. parts of sodium lignin sulfonate, 2 wt. parts of polyvinyl alcohol and 46 wt. parts of fine clay were uniformly mixed and crushed to give a wettable powder.

Composition No. 3 Flowable suspension:

25 Wt. parts of Compound No. 4, 25 wt. parts of Compound B, 10 wt. parts of ethyleneglycolmonobutyl ether, 8 wt. parts of a mixture of polyoxyethylenenonylpheonl ether and polyoxyethylenesorbitanemonobutylate and sodium alkylarylsulfonate, 3 wt. parts of colloidal hydrated aluminum silicate and 29 wt. parts of water were mixed and crushed in wet condition to obtain 100 wt. parts of a uniform flowable suspension.

Composition No. 4: Flowable suspension:

40 Wt. parts of Compound No. 3, 10 wt. parts of Compound A, 10 wt. parts of ethyleneglycol, 3 wt. parts of sodium alkylarylsulfonate, 7 wt. parts of polyoxyethylalkylaryl ether, 2 wt. parts of sodium alkyl naphthalenesulfonate and 28 wt. parts of water were uniformly mixed to obtain a flavorable suspension.

Composition No. 5: Granules:

10 Wt. parts of Compound No. 3, 4 wt. parts of Compound A, 20 wt. parts of bentonite, 2 wt. parts of sodium lignin sulfonate, 1 wt. part of polyvinyl alcohol, and 63 wt. parts of kaolin were crushed and mixed. The mixture was mixed with water; extruded and granulated by an extruder type granulator, and dried and sieved to obtain granules.

Composition No. 6: Wettable powder:

A 19.9 g (0.1 mole) amount of o-methylbenzoyl bromide was added in a dropwise fashion with cooling to a mixture of 13.7 g (0.1 mole) of o-ethoxyaniline and 8.4 g (0.1 mole) of sodium bicarbonate in 200 ml of acetone with stirring. After the addition, the reaction mixture was warmed to 40° C and the mixture was stirred for another 40 hours under reflux. After filtering, ether was distilled from the reaction mixture and the residual material was dissolved in ether again and washed with water. The ether layer was dried over anhydrous sodium sulfate. The ether was evaporated and the product was distilled to obtain 24.1 g (yield of 94.5%) of a clear pink liquid having a boiling point of 148° C/0.04 mmHg and $n_D^{20}$ of 1.5929. IR cm$^{-1}$ (K Br-film) $\nu_{NH}$3295(S), $\nu_{CO}$ 1655, 1615(S).

25 Wt. parts of 2'-ethoxy-2-methylbenzanilide, 25 wt. parts of Compound B, 2 wt. parts of sodium lignin sulfonate, 2 wt. parts of polyvinyl alcohol and 46 wt. parts of fine clay were uniformly mixed and crushed to give a wettable powder.

Composition No. 7: Dust:

13.6 g (0.1 mole) of o-methylbenzoic acid, 15.1 g (0.1 mole) of m-isopropoxyaniline and 10.1 g (0.1 mole) of triethylamine were dissolved in 100 ml of xylene.

5.1 g (0.033 mole) of phosphorus oxychloride was added dropwise to the above solution with stirring at 90° – 100° C. The mixture was then stirred at 90° – 100° C for 3 hours, following which the reaction mixture was cooled and washed with water.

The product was dried over anhydrous sodium sulfate and the xylene was evaporated leaving 20.9 g (yield 77.9%) of white prismic crystals having a melting point of 92° – 94° C.

25 Wt. parts of 3'-iso-proxy-2-methylbenzanilide, 25 wt. parts of Compound A, 0.4 wt. part of tall oil fatty acid, 0.5 wt. part of hydrated silica and 49.1 wt. parts of fine clay were uniformly mixed and crushed to give a dust composition. The effects of the agricultural germicidal compositions of the invention are shown in the experiments below.

Experiment 1

Kidney bean Stem rot Inhibition

Test by Soil drench and injection treatment

*Sclerotinia sclerotiorum* cultured on wheat bran for 20 days was mixed with a soil disinfected with chloropicrin at a ratio of 1 : 10.

The *Sclerotinia sclerotiorum* containing soil was placed in a seedling box (50 cm × 50 cm × 20 cm), and kidney bean seeds were sown at a rate of 80 seeds per one box.

Each of the specific diluted solutions of the wettable powder of Composition No. 2 was drenched at a rate of 3 liter/m²(750 cc/box) 1 day after sowing.

Twenty days after from the sowing, the number of infected seedlings was counted.

$$\text{Percent normally grown seedling} = \frac{\text{number of normally grown seedlings} - \text{number of infected seedlings}}{\text{number of seeds}} \times 100$$

The results are shown in Table 1.

Note:

The amounts of the active ingredients were adjusted with the fine clay in the preparation of the wettable powders.

Table 1

| Active ingredient | | | Concentration in drench (ppm) | Percent sprouting (%) | Percent normally grown seedling (%) | Phytotoxicity (chemical injury) |
|---|---|---|---|---|---|---|
| Compound A | | | 500 | 96.3 | 13.8 | none |
| Compound B | | | " | 95.0 | 0 | " |
| Compound No. 1 | | | " | 98.8 | 0 | " |
| Compound No. 2 | | | " | 97.5 | 16.8 | " |
| Compound 3 | | | " | 93.8 | 0 | " |
| Compound 4 | | | " | 96.3 | 8.8 | " |
| Compound 5 | | | " | 95.0 | 7.5 | " |
| Compound 6 | | | " | 97.5 | 17.5 | " |
| Compound 7 | | | " | 98.8 | 0 | " |
| Compound 8 | | | " | 97.5 | 0 | " |
| Compound | | Compound | | | | |
| A | + | 1 | 50 + 100 | 95.0 | 85.0 | " |
| A | + | 2 | " | 96.3 | 76.2 | " |
| A | + | 3 | " | 98.8 | 83.7 | " |
| A | + | 4 | " | 100 | 100 | " |
| A | + | 5 | " | 100 | 75.0 | " |
| A | + | 6 | " | 100 | 100 | " |
| A | + | 7 | " | 100 | 100 | " |
| A | + | 8 | " | 100 | 81.2 | " |
| B | + | 1 | 50 + 100 | 95.0 | 75.0 | " |
| B | + | 2 | " | 97.5 | 85.0 | " |
| B | + | 3 | " | 96.3 | 90.0 | " |
| B | + | 4 | " | 100 | 100 | " |
| B | + | 5 | " | 96.3 | 72.5 | " |
| B | + | 6 | " | 100 | 100 | " |
| B | + | 7 | " | 100 | 100 | " |
| B | + | 8 | " | 97.5 | 86.2 | " |
| Non-treated | | | — | 95.0 | 0 | " |

Experiment 2

The kidney bean seeds were sown in the *Sclerotinia sclerotiorum* containing soil the same as in Experiment 1.

Ten days after sowing, each of the specific diluted solution of the wettable powder of Composition No. 2 was sprayed onto the foliage of the cotyledons of kidney beans in amounts of 150 cc/m²(37.5 cc/box).

Twenty days after sowing, the number of infected seedlings was counted.

The results are shown in Table 2.

Table 2

| Active ingredients | | | Concentration for spraying (ppm) | Percent sprouting (%) | Percent normally grown seedling (%) | Phytotoxicity (chemical injury) |
|---|---|---|---|---|---|---|
| Compound A | | | 500 | 97.5 | 0 | none |
| | | | 250 | 98.8 | 0 | " |
| Compound B | | | 500 | 95.0 | 0 | " |
| | | | 250 | 96.3 | 0 | " |
| Compound 4 | | | 500 | 98.8 | 10.0 | " |
| | | | 250 | 96.3 | 0 | " |
| Compound 6 | | | 500 | 97.5 | 8.8 | " |
| | | | 250 | 95.0 | 0 | " |
| Compound 7 | | | 500 | 100.0 | 0 | " |
| | | | 250 | 95.0 | 0 | " |
| Compound | | Compound | | | | |
| A | + | 4 | 150 + 300 | 100 | 100 | " |
| | | | 50 + 100 | 100 | 73.8 | " |
| A | + | 6 | 150 + 300 | 100 | 100 | " |
| | | | 50 + 100 | 100 | 100 | " |

Table 2-continued

| Active ingredients | | | Concentration for spraying (ppm) | Percent sprouting (%) | Percent normally grown seedling (%) | Phytotoxicity (chemical injury) |
|---|---|---|---|---|---|---|
| A | + | 7 | 150 + 300 | 100 | 100 | " |
| | | | 50 + 100 | 100 | 88.8 | " |
| B | + | 4 | 150 + 300 | 100 | 100 | " |
| | | | 50 + 100 | 100 | 88.8 | " |
| B | + | 6 | 150 + 300 | 100 | 100 | " |
| | | | 50 + 100 | 100 | 100 | " |
| B | + | 7 | 150 + 300 | 100 | 100 | " |
| | | | 50 + 100 | 98.8 | 83.8 | " |
| Non-treated | | | — | 95.0 | 0 | " |

Experiment 3:

Cotton seedling

Damping-off Inhibition Test

Cotton seeds were treated with a powder of Composition No. 1 (the amounts of the active ingredients were adjusted with the fine clay in the preparation of the powder) and 100 of the treated cotton seeds were sown in each of a series of fields in which cotton seedling damping-off disease caused by Rhizoctonia Solani is usually found, for 50 stubs (4 seeds per one stub). The cotton seedling damping-off disease was naturally caused by Rhizoctonia Solani.

The number of seedlings was counted and also the number of normally grown seedlings after 16 days from the sowing was counted. The percent sprouting and the percent normally grown seedlings were calculated by the equations.

$$\text{Percent sprouting} = \frac{\text{number of sprouted seeds}}{\text{number of seeds sown}} \times 100$$

$$\text{Percent normally grown seedling} = \frac{\text{number of normally grown seedlings}}{\text{number of seedlings}} \times 100$$

The results are shown in Table 3.

Table 3

| Active ingredients | Amount of seed dressing (w/w %) | Percent sprouting (%) | Percent normally grown seedling (%) | Phytotoxicity (chemical injury) |
|---|---|---|---|---|
| Compound A | 0.2 | 63.5 | 37.0 | none |
| | 0.1 | 41.0 | 0 | " |
| Compound B | 0.2 | 44.5 | 36.0 | " |
| | 0.1 | 26.0 | 0 | " |
| Compound 4 | 0.1 | 66.5 | 100 | " |
| | 0.01 | 42.0 | 87.5 | " |
| Compound 6 | 0.1 | 62.0 | 100 | " |
| | 0.01 | 53.5 | 100 | " |
| Compound 7 | 0.1 | 62.5 | 100 | " |
| | 0.01 | 48.0 | 88.0 | " |
| Compound A + Compound 4 | 0.03 + 0.06 | 100 | 100 | " |
| | 0.01 + 0.02 | 100 | 80.5 | " |
| A + 6 | 0.03 + 0.06 | 100 | 100 | " |
| | 0.01 + 0.02 | 100 | 100 | " |
| A + 7 | 0.03 + 0.06 | 100 | 100 | " |
| | 0.01 + 0.02 | 100 | 100 | " |
| B + 4 | 0.03 + 0.06 | 100 | 100 | " |
| | 0.01 + 0.02 | 96.5 | 85.0 | " |
| B + 6 | 0.03 + 0.06 | 100 | 100 | " |
| | 0.01 + 0.02 | 100 | 100 | " |
| B + 7 | 0.03 + 0.06 | 100 | 100 | " |
| | 0.01 + 0.02 | 100 | 100 | " |
| Non-treated | — | 26.0 | 0 | " |

We claim:

1. An agricultural fungicidal composition, which comprises:

one part of a benzanilide of the formula:

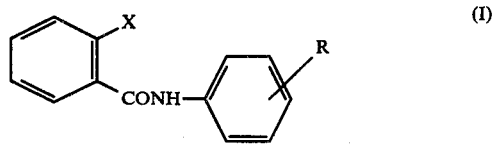

(I)

wherein X represents halogen or methyl and R represents hydrogen, $C_{1-5}$ alkyl or a $C_{1-5}$ alkoxy with from 0.1-10 parts of a phthalimide of the formula:

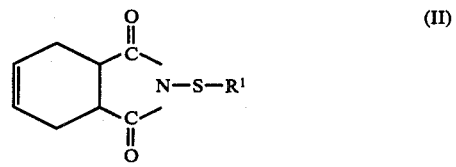

(II)

wherein $R^1$ represents trichloromethyl or 1,1,2,2-tetrachloroethyl as active ingredients.

2. The agricultural fungicidal composition according to claim 1, which comprises a 2-methyl benzanilide compound of the formula

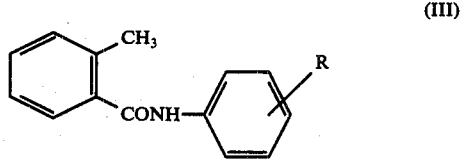

(III)

wherein R represents hydrogen, $C_{1-5}$ alkyl or $C_{1-5}$ alkoxy and a phthalimide of the formula

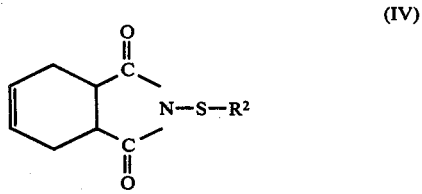

(IV)

wherein $R^2$ represents trichloromethyl or 1,1,2,2-tetrachloroethyl, as active ingredients.

3. The agricultural fungicidal composition according to claim 1, which comprises a 2-halobenzanilide compound of the formula

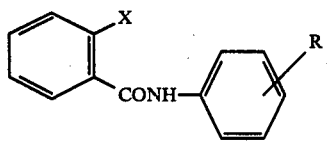
(V)

wherein X represents chlorine, bromine, or iodine and R represents hydrogen, $C_{1-5}$ alkyl or $C_{1-5}$ alkoxy, and a phthalimide of the formula

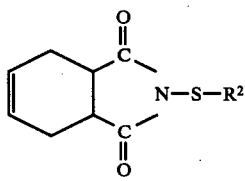

wherein $R^2$ represents trichloromethyl or 1,1,2,2-tetrachloroethyl as active ingredients.

4. The agricultural fungicidal composition according to claim 2, which comprises a 2-methylbenzanilide compound of the formula

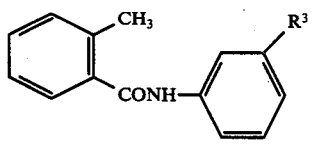

wherein $R^3$ represents $C_{1-5}$ alkyl or $C_{1-5}$ alkoxy and a phthalimide of the formula

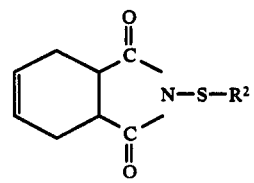

wherein $R^2$ represents trichloromethyl or 1,1,2,2-tetrachloroethyl as active ingredients.

5. The agricultural fungicidal composition according to claim 3, which comprises a 2-iodobenzanilide compound of the formula

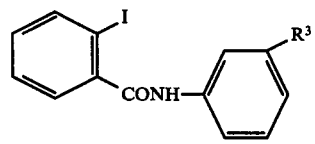

wherein $R^3$ represents $C_{1-5}$ alkyl or $C_{1-5}$ alkoxy and a phthalimide of the formula

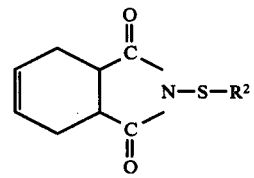

wherein $R^2$ represents trichloromethyl or 1,1,2,2-tetrachloroethyl, as active ingredients.

6. The agricultural fungicidal composition according to claim 1, which comprises either 3' isopropoxyl-2-iodobenzanilide or 3'-isopropoxy-2-methylbenzanilide and N-trichloromethylmethylthio-3a, 4, 4,7a-tetrahydrophthalimide, as the active ingredients.

7. The agricultural fungicidal composition according to claim 1, wherein the composition is in the form of a dust, granule, wettable powder, emulsion, flowable suspension or microcapsule.

8. A method of inhibiting fungus diseases of seeds, soil and plants by applying an effective amount of the agricultural fungicidal composition of claim 1 to said seeds, soil or plants.

* * * * *